US006754353B1

(12) United States Patent
Cheng

(10) Patent No.: US 6,754,353 B1
(45) Date of Patent: Jun. 22, 2004

(54) NON-INTERFERENCE ZONES GENERATED BY ACOUSTIC WAVE CANCELLATION SYSTEM

(75) Inventor: Bruce C. H. Cheng, Taipei (TW)

(73) Assignee: Delta Electronics, Inc., Taipei (TW)

( * ) Notice: Subject to any disclaimer, the term of this patent is extended or adjusted under 35 U.S.C. 154(b) by 0 days.

(21) Appl. No.: 09/382,137

(22) Filed: Aug. 24, 1999

(51) Int. Cl.[7] ......................... A61F 11/06; G10K 11/16; H03B 29/00

(52) U.S. Cl. ....................................... 381/71.1; 704/226

(58) Field of Search ............................ 381/71.1–71.14, 381/94.1–94.9; 704/226, 227, 228, 273, 270

(56) References Cited

U.S. PATENT DOCUMENTS 5,251,263 A * 10/1993 Andrea ...................... 381/71.6
5,889,869 A * 3/1999 Botros ..................... 381/71.11
6,272,360 B1 * 8/2001 Yamaguchi ................ 381/71.4

* cited by examiner

*Primary Examiner*—Minsun Oh Harvey
(74) *Attorney, Agent, or Firm*—Bo-In Lin

(57) ABSTRACT

The present invention discloses an acoustic voice cancellation system for generating a non-interference zone. The acoustic system includes an input transducer for receiving an acoustic input signal from a speaker to a signal processor. The acoustic system further includes a subsystem for providing a non-interfering environment The subsystem for providing non-interfering environment generates an acoustic cancellation signal for destructively interfering with the acoustic input signal at a distance away from the speaker. In a preferred embodiment, the subsystem for providing a non-interfering environment further includes an acoustic attenuation means for generating a cancellation acoustic signal for destructively interfering with the acoustic input signal. In another preferred embodiment, the subsystem for providing a non-interfering environment further includes a signal transmission means for transmitting the cancellation acoustic signal to the distance away from the speaker. In another preferred embodiment, the signal transmission means is provided for transmitting the cancellation acoustic signal with a speed higher than an air sonic speed. In another preferred embodiment, the acoustic system further includes an output transducer for outputting the cancellation acoustic signal.

18 Claims, 2 Drawing Sheets

NON-INTERFERENCE ZONES GENERATED BY ACOUSTIC WAVE CANCELLATION SYSTEM

BACKGROUND OF THE INVENTION

1. Field of the Invention

This invention relates generally to the voice signal processing system and method. More particularly, this invention relates to a new apparatus and method for inputting voice to a voice processing system, such as a computer, which provide adaptive voice cancellation environment whereby interference generated by voice input can be prevented.

2. Description of the Prior Art

A major concern for implementing the speech receivers and processing systems for providing input to the computers, is the noisy environment. Particularly, when many computer users speak to their own computer simultaneously in an enclosed office. Additionally, the concern of privacy may prevent the use of voice input to a computer. For example, sitting on an airplane, the concern for bothering passenger sitting on the nearby seats or more vulnerable for passing out confidential information would hinder the use of a voice input system for a personal or laptop computer.

In U.S. Pat. No. 5,396,561, entitled "Active Acoustic Attenuation and Spectral Shaping System" (issued on Mar. 7, 1995), Popovich et al. disclose an active acoustic system to provide attenuation and spectral shaping of an acoustic wave. Techniques for active attenuation that involves canceling acoustic wave to destructively interfere with and cancel an input acoustic wave are disclosed. In an active acoustic attenuation system, the input acoustic wave is sensed with an error transducer, e.g., a microphone. The transducers then supplies the sensed error signals to a control model to generate a correctional signal. The correctional signal is provided to a canceling transducer such as a loudspeaker to cancel the input acoustic wave. The improvement of this system includes a phase lock loop locked to the input acoustic wave and then generates a desired signal in given phase relation with the input acoustic wave.

This active acoustic attenuation and spectral shaping system is very useful for an acoustic system, which receives voice input and undesirable noises as background information. The adaptive filter can be applied to cancel the noises by producing destructive interference signals. The active acoustic attenuation system as disclosed would be useful for a public announcing (PA) system or an acoustic recording chamber to filtering and canceling the undesirable noises.

However, such as system would not be useful to provide a solution for the difficulties faced by those using speed as an input means to a computer. Because in this situation, a speaker's acoustic waves are propagated simultaneously to the input device and to the surrounding environment. The canceling acoustic wave generated and outputted from a canceling transducer, e.g., a loudspeaker, even with a small time delay, would be lagging behind the original acoustic wave issued from the speaker. Specifically, if the time delay for producing the canceling attenuation signals are $\Delta t$ millisecond, and the sonic speed is S, then the canceling signal waves travel behind the original speaker's voice by distance of $D=S\Delta t$ The canceling signals cannot catch up with the original sound waves from the speaker because both are propagating in the air with the same sonic speed.

Therefore, an acoustic attenuation and cancellation system as discussed above is not too useful for providing a quite environment for operation of multiple voice-input computers. A need still exists to provide a solution to resolve the difficulty of a noisy environment due multiple computer users speaking simultaneously to their own computer for providing voice input.

SUMMARY OF THE PRESENT INVENTION

It is therefore an object of the present invention to provide a novel system configuration for attenuating and canceling voice input to a speech processor propagated to the surrounding space. A non-interfering and private environment can then be provided when acoustic signals are employed as means for providing input data to a computer such that the aforementioned limitations and difficulties encountered in the prior art can be overcome.

Specifically, it is an object of the present invention to provide a novel active acoustic attenuation and cancellation system arranged in a novel acoustic configuration to overcome the difficulty of the prior art The acoustic attenuation signals are first generated then provided to a cancellation transducer at a distance away from the original acoustic source for outputting at a proper time for canceling the original acoustic input propagated to the surrounding environment to that distance.

Another object of the present invention is to provide novel active acoustic attenuation and cancellation system arranged in a novel acoustic configuration by taking advantage of higher speed of signal transmission speed than sonic speed in the air. The cancellation signals are provided to a transducer at distance away from the original acoustic source. The cancellation signals are transmitted to the transducers earlier than the sound wave propagated to that distance. By controlling the time of outputting the cancellation signals at the time when the acoustic waves are propagated to that distance, effective acoustic cancellation can be carried out without affect the clear and precise input to the computers.

Another object of the present invention is to provide novel active acoustic attenuation and cancellation system arranged in a novel acoustic configuration by taking advantage of higher speed of wireless signal transmission than the sonic speed in the air. The cancellation signals are provided to a transducer at distance away from the original acoustic source by wireless signal transmission. The time of outputting the cancellation signals is controlled precisely at the time when the acoustic waves are propagated to that distance. Effective acoustic cancellation can be carried out without affect the clear and precise input to the computers.

Briefly, in a preferred embodiment, the present invention discloses an acoustic system that includes an input transducer for receiving an acoustic input signal from a speaker to a signal processing means. The acoustic system further includes means for providing a non-interfering environment. The means for providing non-interfering environment generates an acoustic cancellation signal for destructively interfering with the acoustic input signal at a distance away from the speaker. In a preferred embodiment, the means for providing a non-interfering environment further includes an acoustic attenuation means for generating a cancellation acoustic signal for destructively interfering with the acoustic input signal. In another preferred embodiment, the means for providing a non-interfering environment further includes a signal transmission means for transmitting the cancellation acoustic signal to the distance away from the speaker. In another preferred embodiment the signal transmission means is provided for transmitting the cancellation acoustic signal with a speed higher than an air sonic speed. In another preferred embodiment, the acoustic system further includes an output transducer for outputting the cancellation acoustic signal.

These and other objects and advantages of the present invention will no doubt become obvious to those of ordinary skill in the art after having read the following detailed description of the preferred embodiment which is illustrated in the various drawing figures.

DETAILED DESCRIPTION OF THE PREFERRED EMBODIMENT

Figure 1:
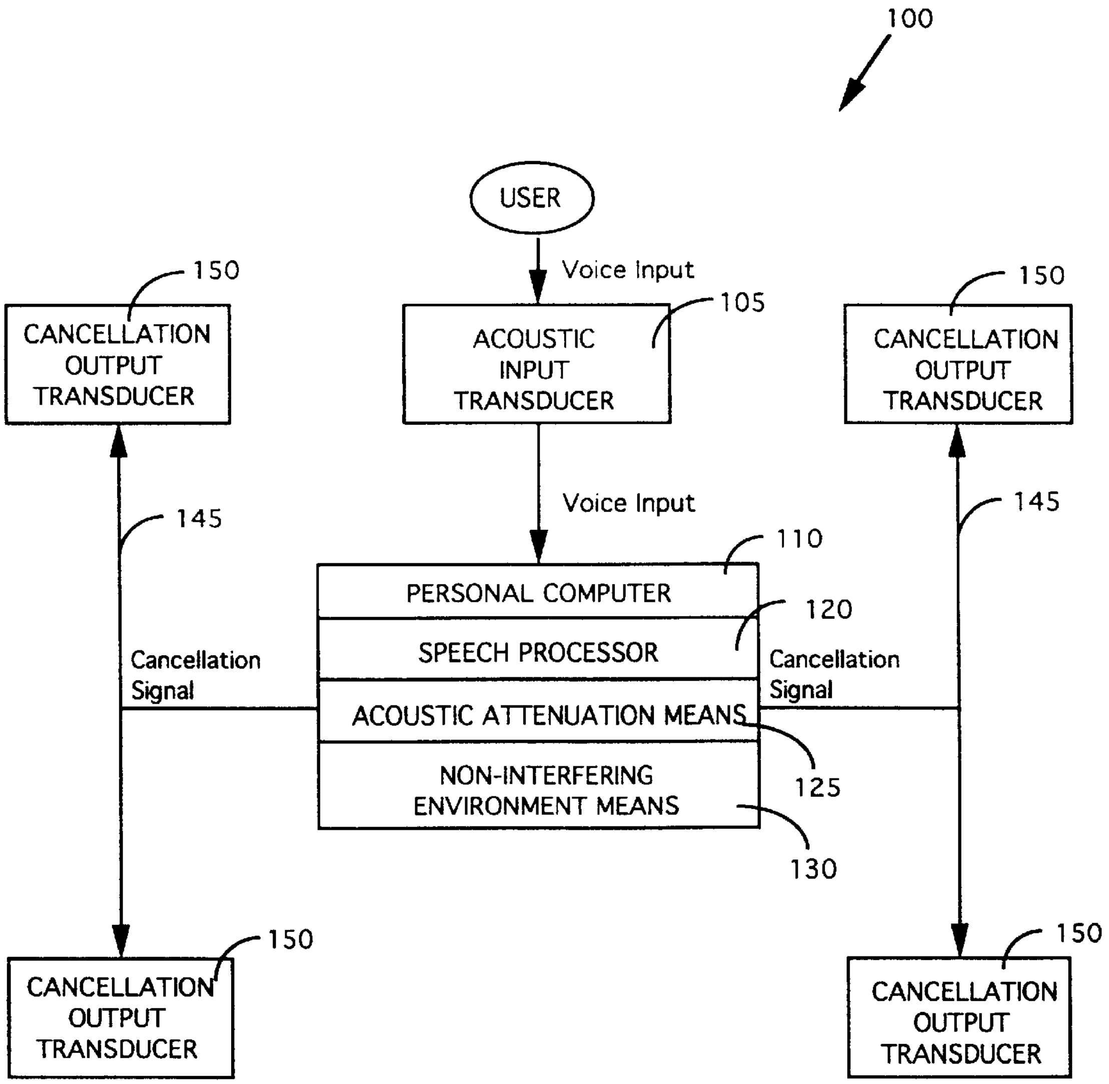
FIG. 1 is a functional block diagram showing the perspective view of an acoustic system of this invention for providing a non-interfering environment.

FIG. 1 is a functional block diagram of the configuration of a new acoustic system 100, which provides a non-interfering environment when a user speaks to a personal computer 110 through a acoustic input transducer 105, e.g., a microphone. The personal computer 110 has a speech processor 120 to process the acoustic input as input data. The user can speak to a computer without requiring to type on a keyboard. Faster and more efficient use of the computer 110 is achieved with the speech processor 120. While the speech processor 120 processes the voice input, an acoustic attenuation means 125 receives the acoustic input to generate acoustic cancellation signals. The system as that disclosed in U.S. Pat. No. 5,396,561, entitled "Active Acoustic Attenuation and Spectral Shaping System" (issued on Mar. 7, 1995), Popovich et al. can be implemented for the acoustic attenuation means 125 to generate the cancellation signal for destructively interfering with the acoustic input from the user. The subject matters disclosed and described in U.S. Pat. No. 5,396,561 and associated U.S. Pat. Nos. 4,677,676, 4,677,677, 4,736,431, 4,815,139, 4,837,834, 4,987,598, 5,022,082, and 5,033,082, are incorporated herein by reference.

The acoustic system 100 further includes a means for providing a non-interfering environment 130, which controls the transmission of the cancellation signal through the transmission lines 145, from the acoustic attenuation means 125 to the cancellation output transducer 150. The cancellation output transducers 150 are located at a certain distance away from the acoustic input transducer 105. The sound waves generated from the user when speech utterances are inputted to the acoustic input transducer 105 also are propagated at a sonic speed in the air. The means for providing a non-interfering environment 130 also controls the transmission time and the time for generating acoustic output from the cancellation transducers 150 to destructively interfering with the sound waves propagated near the output transducer 150. By carefully arranging the cancellation output transducers, the sound waves generated from user's speech input to the personal computer 110 are significantly canceled. A non-interfere environment is provided outside of the area substantially surrounded by the cancellation output transducers 150. The transmission lines 145 for transmitting the cancellation signals can be signal wires with high-speed signal transmission if required. As the signal transmission over the transmission lines are generally faster than the sonic speed in the air, it can be conveniently control to transmit the acoustic cancellation signal to the cancellation acoustic output transducers 150 well ahead of the arrival of the acoustic sound waves. Proper timing can be arranged to activate the acoustic cancellation signals that have opposite phase with the sound waves propagated through the air. Destructive interference with the sound waves is achieved to eliminate further propagation of the sound waves outside of the areas covered by substantially by the cancellation output transducers 150.

Figure 2:
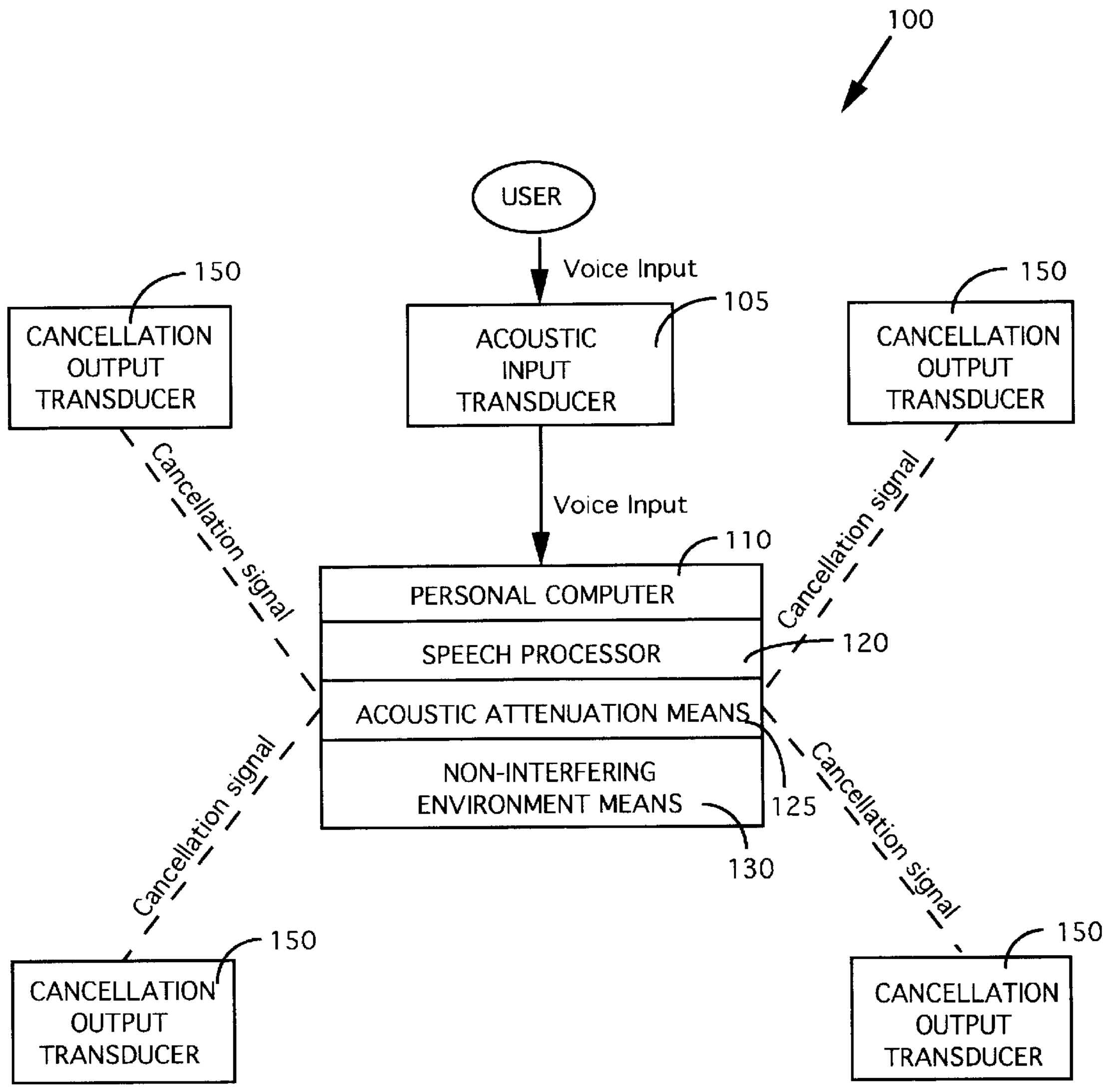
FIG. 2 is a functional block diagram showing the perspective view of an acoustic system of another preferred embodiment of this invention for providing a non-interfering environment.

FIG. 2 is a functional block diagram of an acoustic system, which is essentially the same as that shown in FIG. 1. The only difference is the cancellation signals are transmitted through a wireless signal transmission means. The cancellation signal may be a RF signals generated from a RF transmitter located in the means for providing non-interfering environment 130. A RF receiver is then placed in the cancellation output transducer 150 to receive the cancellation signal for generating attenuating cancellation signals to destructively interfere with the sound waves propagated from the user to the area near the output transducers 150.

According to FIGS. 1 and 2 and above description, this invention discloses an acoustic system 100. The acoustic system 100 includes an input transducer 105 for receiving an acoustic input signal from a speaker to a signal processing in means 125. The acoustic system further includes means for providing a non-interfering environment 130. The means for providing non-interfering environment 130 generates an acoustic cancellation signal for destructively interfering with the acoustic input signal at a distance away from the speaker. In a preferred embodiment, the means for providing a non-interfering environment 130 further includes an acoustic attenuation means 125 for generating a cancellation acoustic signal for destructively interfering with the acoustic input signal. In another preferred embodiment, the means for providing a non-interfering environment 130 further includes a signal transmission means 145 for transmitting the cancellation acoustic signal to the distance away from the speaker. In another preferred embodiment, the signal transmission means 145 is provided for transmitting the cancellation acoustic signal with a speed higher than an air sonic speed. In another preferred embodiment, the acoustic system 100 further includes an output transducer 150 for outputting the cancellation acoustic signal.

According to the disclosure of this invention, a method for providing a non-interfering environment for an acoustic system is taught. The method includes steps of a) providing an input transducer for receiving an acoustic input signal from a speaker to a signal processing means. And, b) generating an acoustic cancellation signal for destructively interfering with the acoustic input signal at a distance away from the speaker. In a specific embodiment, the step of providing a non-interfering environment further includes a step of providing an acoustic attenuation means for generating a cancellation acoustic signal for destructively interfering with the acoustic input signal. In another specific embodiment, the step of for providing a non-interfering environment further includes a step of providing signal transmission means for transmitting the cancellation acoustic signal to the distance away from the speaker. In another preferred embodiment, the step of providing a signal transmission means is a step of providing a signal transmission means for transmitting the cancellation acoustic signal with a speed higher than an air sonic speed. In another preferred embodiment, the method further includes a step of c) providing an output transducer for outputting the cancellation acoustic signal.

The present invention therefore provides a novel system configuration for attenuating and canceling voice input to a speech processor propagated to the surrounding space. A non-interfering and private environment can then be provided when acoustic signals are employed as means for providing input data to a computer such that the limitations and difficulties encountered in the prior art are overcome. Specifically, a novel active acoustic attenuation and cancellation system arranged in a novel acoustic configuration is implemented to overcome the difficulty of the prior art The acoustic attenuation signals are first generated then provided to a cancellation transducer at a distance away from the original acoustic source for outputting at a proper time for canceling the original acoustic input propagated to the surrounding environment to that distance. The cancellation signals are controlled and arranged to transmit to the transducers earlier than the sound wave propagated to that distance. By controlling the time of outputting the cancellation signals at the time when the acoustic waves are propagated to that distance, effective acoustic cancellation can be carried out without affect the clear and precise input to the computers. The time of outputting the cancellation signals is controlled precisely at the time when the acoustic waves are propagated to that distance. Effective acoustic cancellation is carried out without affect the clear and precise input to the computers.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

I claim:

1. An acoustic system for reducing acoustic signals transmitting outside of a private zone comprising:

a signal processing means includes an input transducer for receiving an acoustic input signal from an acoustic source disposed substantially in a mid portion of said private zone; and said signal processing means further includes an acoustic attenuation means disposed in and integrated as part of said signal processing means for generating an acoustic cancellation signal directly from and corresponding to an acoustic signal propagated to a peripheral point of said private zone from said acoustic input signal for destructively interfering with said acoustic input signal propagated to said peripheral point of said private zone at a distance away from said acoustic source.

2. The acoustic system of claim 1 wherein:

said signal processing means further includes a speech processing means for processing said acoustic input signal received from said acoustic source as a speech message data.

3. The acoustic system of claim 2 further comprising:

a signal transmission means for transmitting said acoustic cancellation signal to said distance away from said acoustic source at a higher speed higher than an air sonic speed as said acoustic input signal propagated to said peripheral point of said private zone.

4. The acoustic system of claim 1 wherein:

said acoustic attenuation means is provided for generating electromagnetic signals directly from and corresponding to said acoustic signal propagated to said peripheral point of said private zone from said acoustic input signal ready for generating said acoustic cancellation signal for destructively interfering with said acoustic signal propagated to said peripheral point of said private zone from said acoustic input signal at a distance away from said acoustic source.

5. The acoustic system of claim 1 further comprising:

an output transducer disposed at said peripheral point of said private zone at said distance away from said acoustic source for receiving said acoustic cancellation signal from said signal processing means for outputting said acoustic cancellation signal.

6. A method for reducing acoustic signals from transmitting out of a private zone surrounding an acoustic system comprising:

providing an input transducer for receiving an acoustic input signal from an acoustic source to a signal processing means with said acoustic source disposed in a mid portion of said private zone; and integrating an acoustic attenuation means as part of said signal processing means for generating an acoustic cancellation signal directly from and corresponding to an acoustic signal propagated to a peripheral point of said private zone from said acoustic input signal for destructively interfering with said acoustic signal propagated to said peripheral point of said private zone from said acoustic input signal at a distance away from said acoustic source.

7. The method of claim 6 further comprising a step of:

providing a speech processing means for processing said acoustic input signal received from said acoustic source as a speech message data.

8. The method of claim 6 further comprising:

providing signal transmission means for transmitting said acoustic cancellation signal to said peripheral point of said private zone at a distance away from said acoustic source at a higher speed higher than an air sonic speed as said acoustic signal propagated to said peripheral point of said private zone.

9. The method of claim 6 wherein:

said step of generating said acoustic cancellation signal further comprising a step of generating electromagnetic signals directly from and corresponding to said acoustic signal propagated to said peripheral point of said private zone from said acoustic input signal ready for generating said acoustic cancellation signal for destructively interfering with said acoustic signal propagated to said peripheral point of said private zone from said acoustic input signal at a distance away from said acoustic source.

10. The method of claim 9 further comprising a step of:

disposing an output transducer at said peripheral point of said private zone at said distance away from said acoustic source for receiving said electromagnetic signal from said signal processing means for outputting said acoustic cancellation signal.

11. A data handling system comprising:

an input transducer for receiving an acoustic input signal from an acoustic source disposed in a mid portion of a private zone surrounding said data handling system;

a signal processing means for processing and converting said acoustic input signal into electromagnetic signals for said data handling system; and said signal processing means further includes a means for generating an acoustic cancellation signal directly from and corresponding to an acoustic signal propagated to a peripheral point of said private zone from said acoustic input signal for destructively interfering with said acoustic signal propagated to said peripheral point of said private zone from said acoustic input signal at a distance away from said acoustic source.

12. The data handling system of claim 11 wherein:

said signal processing means further includes a speech processing means for processing said acoustic input signal received from said acoustic source as a speech message data.

13. The data handling system of claim 11 further comprising:

a signal transmission means for transmitting said acoustic cancellation signal to said distance away from said acoustic source at a higher speed higher than an air sonic speed as said acoustic input signal propagated to said peripheral point of said private zone.

14. The data handling system of claim 11 wherein:

said acoustic attenuation means is provided for generating electromagnetic signals directly from and corresponding to said acoustic signal propagated to said peripheral point of said private zone from said acoustic input signal ready for generating said acoustic cancellation signal for destructively interfering with said acoustic signal propagated to said peripheral point of said private zone from said acoustic input signal at a distance away from said acoustic source.

15. The data handling system of claim 11 further comprising:

an output transducer disposed at said peripheral point of said private zone at said distance away from said acoustic source for receiving said acoustic cancellation signal from said signal processing means for outputting said acoustic cancellation signal.

16. The data handling system of claim 11 further comprising:

a personal computer having a central processing unit (CPU) provided to function as said signal processing means.

17. The data handling system of claim 11 further comprising:

a notebook computer having a central processing unit (CPU) provided to function as said signal processing means.

18. The data handling system of claim 11 further comprising:

a personal digital assistant (PDA) device having a data processor provided to function as said signal processing means.

* * * * *